(12) United States Patent
Cantor

(10) Patent No.: US 7,541,140 B2
(45) Date of Patent: *Jun. 2, 2009

(54) ASSESSING RISK FOR KIDNEY STONES USING PARATHYROID HORMONE AGONIST AND ANTAGONIST

(75) Inventor: Thomas L. Cantor, El Cajon, CA (US)

(73) Assignee: Scantibodies Laboratory, Inc., Santee, CA (US)

( * ) Notice: Subject to any disclaimer, the term of this patent is extended or adjusted under 35 U.S.C. 154(b) by 364 days.

This patent is subject to a terminal disclaimer.

(21) Appl. No.: 11/144,437

(22) Filed: Jun. 3, 2005

(65) Prior Publication Data

US 2006/0035282 A1 Feb. 16, 2006

Related U.S. Application Data

(60) Provisional application No. 60/576,552, filed on Jun. 3, 2004.

(51) Int. Cl.
*C12Q 1/00* (2006.01)
*A61K 49/00* (2006.01)
*A61K 38/00* (2006.01)
*G01N 33/00* (2006.01)

(52) U.S. Cl. ............................ 435/4; 436/86; 424/9.1; 514/12

(58) Field of Classification Search ................. None
See application file for complete search history.

(56) References Cited

U.S. PATENT DOCUMENTS

| | | | |
|---|---|---|---|
| 4,086,196 A | 4/1978 | Tregear | |
| 4,656,250 A | 4/1987 | Morita et al. | |
| 4,968,669 A | 11/1990 | Rosenblatt et al. | |
| 5,093,233 A | 3/1992 | Rosenblatt et al. | |
| 5,208,041 A | 5/1993 | Sindrey | |
| 5,317,010 A | 5/1994 | Pang et al. | |
| 5,382,658 A | 1/1995 | Kronis et al. | |
| 5,434,246 A | 7/1995 | Fukuda et al. | |
| 5,496,801 A | 3/1996 | Holthuis et al. | |
| 5,589,452 A | 12/1996 | Krstenansky et al. | |
| 5,695,955 A | 12/1997 | Krstenansky et al. | |
| 5,723,577 A | 3/1998 | Dong | |
| 5,747,456 A | 5/1998 | Chorev et al. | |
| 5,783,558 A | 7/1998 | Duvos et al. | |
| 5,798,225 A | 8/1998 | Krstenansky et al. | |
| 5,807,823 A | 9/1998 | Krstenansky et al. | |
| 5,840,831 A | 11/1998 | Hamachi et al. | |
| 5,849,695 A | 12/1998 | Cohen et al. | |
| 6,689,566 B1 | 2/2004 | Cantor et al. | |
| 6,743,590 B1 | 6/2004 | Cantor et al. | |
| 6,838,264 B2 * | 1/2005 | Zahradnik et al. | 435/70.21 |
| 2002/0110871 A1 | 8/2002 | Zahradnik et al. | |
| 2005/0170443 A1 * | 8/2005 | Cantor | 435/7.92 |

OTHER PUBLICATIONS

Williams CP, Child DF, Hudson PR, De Soysa L, Davies GK, Davies MG, De Bolla AR. (1996) Inappropriate phosphate excretion in idiopathic hypercalciuria: the key to a common cause and future treatment? J Clin Pathol 49: pp. 881-888.*
Lepage R, Roy L, BrossardJ-H, Rousseau L, Dorais C, Lazure C, and D'Amour P. (1998) A non-(1-84) circulating parathyroid hormone (PTH) fragment interferes significantly with intact PTH commercial assay measurements in uremic samples. Clin Chem 44: 805-809.*
Peacock M (Nov. 2002) Primary hyperparathyroidism and the kidney: biochemical and clinical spectrum. J Bone Min Res, vol. 17, supplement 2, pp. N87-N94.*
Bushinsky DA et al (2000) Calcium phosphate supersaturation regulates stone formation in genetic hypercalciuric stone-forming rats. Kidney Int, vol. 57, pp. 550-560.*
Chau H et al (Apr. 2003) Renal calcification in mice homozygous for the disrupted Type IIa Na/Pi cotransporter gene Npt2. J Bone Min Res, vol. 18, No. 4, pp. 644-657.*
Sneddon WB et al (published online Aug. 14, 2003) Activation-independent parathyroid hormone receptor internalization is regulated by NHERF1 (EBP50). J Biol Chem, vol. 278, No. 44, pp. 43787-43796.*
Murer H et al (1999) Posttranslational regulation of the proximal tubule NaPi-II transporter in response to PTH and dietary Pi. Am J Physiol Renal Physiol, vol. 277, (Renal Physiol vol. 46,) pp. F676-F684.*
Biochemistry, Stryer ed., 2nd ed. (1981) pp. 13-15.
Bringhurst et al., Hormones and Disorders of Mineral Metabolism, in Williams Textbook of Endocrinology, 10th ed., (2003) p. 1309.
Caetano et al., Equus Genome Res. (1999) 9(12):1239-1249.
Divieti et al., Endocrinology (2002) 143(1):171-176.
Friedman and Gesek, Physiol. Rev. (1995) 75:429-471.
Henikoff et al., PNAS (1992) 89:10915-10919.
Integration of Renal Mechanisms, in Medical Physiology, Guyton and Hall eds., 10th ed. (2000) p. 343.
Lei et al., J. Biol. Chem. (1995) 270(20):11882-11886.
Nguyen-Yamamoto et al., Endocrinology (2001) 142(4):1386-1392.
Nissenson et al., J. Biol. Chem. (1988) 263(26):12866-12871.
Slatopolsky et al., Kidney Int. (2000) 58:753-761.
Sneddon et al., J. Biol. Chem. (2003) 278(44):43787-43796.
Stewart et al., J. Clin. Invest. (1988) 81(2):596-600.
Stoller, Urinary Stone Disease, in Smith's General Urology, Tanagho and McAninch, eds., 16th ed. (2004) pp. 256-274.
Thompson et al., PNAS USA (1988) 85(15):5673-5677.
Watson et al., Molecular Biology of the Gene, Benjamin/Cummings Pub. Co., 4th ed. (1987) p. 224.
Yates et al., J. Clin. Invest. (1988) 81(3):932-938.

* cited by examiner

*Primary Examiner*—Lisa J Hobbs
(74) *Attorney, Agent, or Firm*—Morrison & Foerster LLP

(57) ABSTRACT

The present invention relates to identifying the risk of a subject developing renal stones utilizing an assessment of PTH agonist, antagonist and/or total PTH levels, optionally together with an assessment of serum and/or urine calcium levels and/or other analytes. The present description further relates to monitoring and guiding treatment for renal stones and kits useful therefore.

14 Claims, No Drawings

ASSESSING RISK FOR KIDNEY STONES USING PARATHYROID HORMONE AGONIST AND ANTAGONIST

CROSS-REFERENCE TO RELATED APPLICATIONS

This application claims the priority benefit of the provisional patent application U.S. Ser. No. 60/576,552, filed Jun. 3, 2004, which is incorporated herein by reference in its entirety.

TECHNICAL FIELD

The present invention relates to identifying the risk of a subject developing renal stones. The present description further relates to monitoring and guiding treatment for renal stones.

BACKGROUND

Renal and ureteral stone disease comprises a fairly common disorder of the urinary tract with detrimental consequences to the afflicted patient ranging in degrees of severity. Often referred to as varying forms of nephrolithiasis, this disorder is often characterized, in part, based on the composition of the stone formed in the kidney or ureter. If left untreated, a renal stone can cause damage to the kidneys and potentially lead to kidney failure, among other maladies.

Although the etiology of nephrolithiasis remains elusive, several aspects of the process of stone formation are known. Supersaturated urine is generally required for stone formation, which itself is known to depend on urinary pH, ionic strength, solute concentration and complexation, among other factors. See M. J. Stoller, *Urinary Stone Disease*, in SMITH'S GENERAL UROLOGY 256-262 (E. A. Tanagho & J. W. McAninch eds., 16$^{th}$ ed. 2004). Moreover, a variety of ions and solutes can contribute to stone formation (e.g., calcium, oxalate, phosphate, uric acid, sodium, etc.), with calcium being the major ion present in urinary crystals. Generally, 80%-85% of all renal stone patients have calcareous renal stones. See id. at 257, 259. Although a variety of factors affect the probability of renal stone formation, having an increased concentration of calcium ions in urine (e.g., hypercalciuria) will likewise increase the probability of the formation of stones.

In general, almost all (i.e., between about 95%-99%) of the calcium filtered at the glomerulous is reabsorbed between the proximal tubules, the loop of Henle and the distal and collecting tubules. The distal tubule cells are known to be responsible for the retention and excretion of calcium (to maintain calcium hemostasis). In normal conditions, calcium that is not reabsorbed into the blood stream is excreted in the urine. When lower concentrations of filtered calcium are reabsorbed, there is an increase in the calcium ion concentration in the urine, thus increasing the likelihood of the formation of renal stones.

It has interestingly been recognized that subjects who develop renal stones at one point, and are optionally treated for them, are at an increased risk of developing stones again. Recurrence rates in these subjects are as high as 50-60%, or more.

Early detection of an increased risk of stone formation would permit the institution of preventative and conciliatory measures such as increased water consumption, diet modification (e.g., avoiding foods rich in calcium and/or avoiding the consumption of foods high in oxalates such as cola, coffee, chocolate, nuts, spinach, strawberries, wheat bran, tea, etc.) or beginning medical treatment. Moreover, as the reoccurrence of renal stones in individual patents is high, it is important to have advance indicators for the progress of treatment modalities to ensure appropriate tailoring and success.

Accordingly, there exists a need in the art for early and accurate identification of the risk of developing renal stones in a subject. The present invention addresses this and other related needs in the art.

DISCLOSURE OF THE INVENTION

In leading to the present disclosure it was recognized that because of the differential roles that the proximal and distal tubule cells play in calcium retention and excretion, factors that affect this differential control on these cells are important to detect in order to diagnose the probability of forming renal stones. In one embodiment, the present disclosure is directed to a method for determining the risk of a subject for developing renal calcium calculi comprising: a) determining the presence or level of a PTH antagonist in a sample obtained from a subject; and b) determining the risk for developing renal calcium calculi in the subject based on the presence or level of the PTH antagonist. The risk determination is frequently utilized to monitor and/or guide treatment for renal calculi.

In another embodiment, the present disclosure is directed to a method for determining the risk of a subject for developing renal calcium calculi comprising: a) determining the level of parathyroid hormone (PTH) agonist and the level of PTH antagonist in a sample obtained from a subject; b) comparing the level of PTH agonist and PTH antagonist in the sample in a ratio; and c) determining the risk for developing renal calcium calculi in the subject based on the ratio. The risk determination is frequently utilized to monitor and/or guide treatment for renal calculi.

In yet another embodiment, the present disclosure is directed to a kit for determining the risk of a subject for developing renal calculi comprising: a) means for determining the level of a PTH antagonist in a sample obtained from a subject; and b) means for evaluating the level of the PTH antagonist and determining the risk of the subject for developing renal calculi. The renal stones frequently comprise renal calcium calculi. In another frequent embodiment, the kit contains means used to determine the ratio of PTH agonist versus PTH antagonist in the subject. In a further frequent embodiment, the kit contains means for measuring and/or comparing any one or more of a variety of variables discussed and contemplated herein.

DETAILED DESCRIPTION OF THE INVENTION

For clarity of disclosure, and not by way of limitation, the detailed description of the invention is divided into the subsections that follow.

A. Definitions

Unless defined otherwise, all terms of art, notations and other scientific terms or terminology used herein have the same meaning as is commonly understood by one of ordinary skill in the art to which this invention belongs. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "renal calcium calculi" refers to renal stones having at least some calcium content.

As used herein, "renal stone(s)" refers to any of the assorted types of urinary, renal, uretal or kidney stones or calculi. These stones may or may not have calcium as a component. See, e.g., M. J. Stoller, *Urinary Stone Disease*, in SMITH'S GENERAL UROLOGY 256 (E. A. Tanagho & J. W. McAninch eds., 16$^{th}$ ed. 2004). Renal calcium calculi comprise one form of renal stones. Unless specifically indicated herein, the terms "renal stones," "kidney stones," "renal calculi" and "uretal stones" are considered equivalent. Although the plural forms of these terms are generally utilized herein, they are intended to encompass stone formations of single and multiple stones/calculi.

As used herein, "renal stone disease" refers to kidney, urinary or uretal stone disease, nephrolithiasis, idiopathic calculous disease or other diseases or disorders that involve renal stone formation.

As used herein, "antibody" is used in the broadest sense. Therefore, an "antibody" can be naturally occurring or manmade such as monoclonal antibodies produced by conventional hybridoma technology. Antibodies of the present invention comprise monoclonal and polyclonal antibodies as well as fragments containing the antigen-binding domain and/or one or more complementarity determining regions of these antibodies. Moreover, "antibody" refers to a polypeptide substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies or fragment thereof made by recombinant methods.

As used herein, "monoclonal antibody" refers to an antibody obtained from a population of substantially homogeneous antibodies, i.e., the antibodies comprising the population are identical except for possible naturally occurring mutations that are present in minor amounts.

As used herein, "polypeptide" refers to a polymer of at least about 4, 5, 6, 7, or 8 amino acids. Throughout the specification, standard three letter or single letter designations for amino acids are used. In the art, this term is often used interchangeably with "peptide" or "protein."

As used herein, "whole parathyroid hormone" or "whole PTH" refers to the complete molecule of PTH or a variant, fragment, derivative or analog thereof. Often this molecule stimulates osteoclast formation, osteoblast formation, bone resorption, stimulation of adenylate cyclase and bone turnover to increase blood calcium levels. 1-84 PTH is an example of whole PTH. For purposes herein, the name "parathyroid hormone (PTH)" is used, although all other names are contemplated. See, e.g., Watson et al., MOLECULAR BIOLOGY OF THE GENE 224 (The Benjamin/Cummings Pub. Co., 4$^{th}$ ed. 1987). Other names of PTH include, for example, parathormone and parathyrin. Whole PTH assay values may be obtained by measuring a sample with a variety of assays. Whole PTH refers to any of a variety of species dependent forms of the PTH molecule. See, e.g., Caetano, A. R., et al., *Equus Genome Res.* 9(12): 1239-1249 (1999) (horse), U.S. patent application Publication US 2002/0110871 A1 (rat, mouse, bovine, canine, porcine), U.S. Pat. Nos. 6,689,566 and 6,743,590 (human).

As used herein, "parathyroid hormone agonist" or "PTH agonist" refers to the complete molecule of PTH or a variant, fragment, derivative or analog thereof. Often this molecule stimulates osteoclast formation, osteoblast formation, bone resorption, stimulation of adenylate cyclase and bone turnover to increase blood calcium levels. Whole PTH, e.g., 1-84 PTH, is an example of a PTH agonist, but other PTH agonists are contemplated. A PTH agonist further refers to peptides which have PTH agonist properties. It is intended to encompass a PTH agonist with conservative amino acid substitutions that do not substantially alter its biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., MOLECULAR BIOLOGY OF THE GENE, cited supra).

As used herein, "parathyroid hormone antagonist" or "PTH antagonist" refers to a PTH fragment or derivative having biological actions that counter all or part of the effects of a PTH agonist, and/or has its own biological activity independent of a PTH agonist. 7-84 PTH is an example of a PTH antagonist. As further described below, a variety of other examples of PTH antagonists are contemplated. This term frequently includes a PTH fragment or derivative that lacks PTH agonist biological activity. It is intended to encompass a PTH antagonist with conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al. MOLECULAR BIOLOGY OF THE GENE, cited supra).

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E), and vice versa; glutamine (Q) for asparagine (N) and vice versa; and serine (S) for threonine (T), and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments. See, e.g., BIOCHEMISTRY 13-15 (L. Stryer ed., 2d ed. 1981); Henikoff et al., *PNAS* (1992) 89:10915-10919; Lei et al., *J. Biol. Chem.* (1995) 270 (20):11882-6.

As used herein, the terms "total PTH" refers to a combination of whole PTH and PTH fragments in a subject. Alternatively, "total PTH" refers to a combination of PTH agonist and PTH antagonist in a subject. Often this "combination" refers to a measurement of the levels of each of the substitutents of the total PTH in a subject.

As used herein, "treatment" means any manner in which the symptoms of a condition, disorder or disease are ameliorated or otherwise beneficially altered. Treatment also encompasses any pharmaceutical use of the compositions herein. Non-pharmaceutical and/or noninvasive "treatment" is also contemplated.

As used herein, "disease or disorder" refers to a pathological condition in an organism resulting from, e.g., infection or genetic defect, and characterized by identifiable symptoms. Frequently, the disease or disorder does not comprise primary hyperparathyroidism.

As used herein, the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues comprise an aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, the term "subject" is not limited to a specific species or sample type. For example, the term "subject" may refer to a patient, and frequently a human patient. However, this term is not limited to humans and thus encompasses a variety of mammalian species. In a frequent embodiment, the subject is not suspected of being afflicted with or does not have primary hyperparathyroidism.

As used herein, the term "specifically binds" refers to the binding specificity of a specific binding pair. Recognition by an antibody of a particular target in the presence of other potential targets is one characteristic of such binding. "Binding component member" refers to a member of a specific binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the binding component pair are referred to as ligand and receptor (antiligand), specific binding pair (sbp) member and sbp partner, and the like. A molecule may also be a sbp member for an aggregation of molecules; for example an antibody raised against an immune complex of a second antibody and its corresponding antigen may be considered to be an sbp member for the immune complex.

B. Parathyroid Hormone and Renal Stones

In leading to the present disclosure it was recognized that whole parathyroid hormone (1-84 PTH) and other PTH ago-nists affect calcium reabsorption in the kidney. Although not intending to be bound by theory, 1-84 PTH stimulates reabsorption of calcium in the loop of Henle and the distal and collecting tubules. See, e.g., *Integration of Renal Mechanisms*, in MEDICAL PHYSIOLOGY 343 (A. C. Guyton & J. E. Hall eds., 10$^{th}$ ed. 2000); F. Bringhurst et al., *Hormones and Disorders of Mineral Metabolism*, in WILLIAMS TEXTBOOK OF ENDOCRINOLOGY 1309 (10$^{th}$ ed. 2003). Thus, increasing concentrations of 1-84 PTH lead to the reabsorption of higher concentrations of calcium. In contrast, calcium reabsorption into the bloodstream is decreased in the absence of, or in the presence of lower concentrations of, 1-84 PTH, thus promoting excretion of increased concentrations of calcium. See id.

Although not intending to be bound by any particular theory, the 1-84 PTH/PTHrp receptor is the receptor responsible for 1-84 PTH-mediated regulation of calcium reabsorption and excretion in the kidney. Thus, binding of 1-84 PTH with and activation of this receptor triggers the reabsorption of calcium from the glomerulous filtrate. Similarly, it has been demonstrated that other PTH agonists such as 1-34 PTH also positively affect calcium reabsorption. See Nguyen-Yamamoto et al., *Endocrinology* (2001) 142(4):1386-92.

It has also been recently demonstrated that the PTH antagonist—7-84 PTH effects internalization, and ultimately leads to a down regulation, of the 1-84 PTH/PTHrp receptor, without concomitant activation. See Sneddon et al., *J. Biol. Chem.* (2003) 278(44):43787-96. In addition, 7-84 PTH, in its role as a competitive antagonist of 1-84 PTH, generally binds and activates a C-terminal receptor independent of the PTH/PTHrp receptor. See P. Divieti, et al., *Endocrinology* (2002) 143(1):171-6. Similarly, PTH antagonists in addition to 7-84 PTH (e.g., 39-84 PTH and 53-84 PTH) also can bind and activate this C-terminal receptor. See Nguyen-Yamamoto et al., supra. 7-84 PTH has been demonstrated to effect a decrease in serum calcium levels through the C-terminal receptor, the PTH/PTHrp receptor, or a combination thereof. See E. Slatopolsky, et al., *Kidney Int.* (2000) 58:753-61. As also indicated in the Slatopolsky (2000) article, serum calcium levels decreased in response to an administration of 7-84 PTH, and this reduction was less than that observed in the controls, which received no PTH (1-84 PTH or 7-84 PTH) stimulation. See id. at 757.

In leading to the present disclosure it was further recognized that PTH antagonists such as 7-84 PTH act to reduce reabsorption of calcium from the glomerulous filtrate. The down regulation of the PTH/PTHrp receptor blunts the action of 1-84 PTH on calcium reabsorption in the loop of Henle and the distal and collecting tubules. Similarly, PTH antagonists, including 7-84 PTH, have been shown to limit the in vivo calcemic responses to 1-84 PTH and 1-34 PTH. See Nguyen-Yamamoto et al., supra. Moreover, the independent action of 7-84 PTH in the kidney further decreases the reabsorption of calcium therein. Thus, the present disclosure recognizes that a reduction of serum calcium following administration (or otherwise increasing or increased in vivo concentrations) of 7-84 PTH would be accompanied by an increase in urinary calcium levels. Accordingly, as 1-84 PTH operates through the 1-84 PTH1/PTHrp receptor, there are at least two factors that are able to affect the reabsorption, or lack thereof (which would lead to the formation of kidney stones), of calcium in the kidney—(1) the level of 1-84 PTH, and (2) the up or down regulation of the 1-84 PTH/PTHrp receptor. Therefore, factors that control the up or down regulation of the 1-84 PTH/PTHrp receptor are important in diagnosing the probability of forming kidney stones. The present disclosure recognizes the importance of monitoring PTH antagonist levels, particularly 7-84 PTH levels, as an assessment for determining the risk of development of or having renal stones in a particular subject.

Another factor that may be evaluated in the determination of the risk of developing renal stones in a subject is accounting for the adaptor protein Na/H exchange regulatory factor 1 (NHERF1) (ezrin-binding protein 50 (EBP50)) scaffolding protein expression. This protein has been shown to protect the PTH1/PTHrp receptors in the proximal tubule cells from degradation or down regulation by 7-84 PTH. See Sneddon et al., *J. Biol. Chem.* (2003) 278(44):43787-96. Although not bound by theory, functional expression of this protein may lead to a decrease in the effect of PTH antagonist on calcium reabsorbtion from the kidney and the attendant risk of developing renal calcium stones.

PTH antagonists that have activity levels similar to 7-84 PTH have been previously described. The present disclosure recognizes that these PTH antagonists will also yield the same or similar effects in the kidney with respect to calcium reabsorption as those described herein for 7-84 PTH. These PTH antagonists are referred to herein as PTH antagonists, and are inclusive of 7-84 PTH. Such PTH antagonists frequently include C-terminal PTH fragments generically described as comprising a contiguous portion of human PTH having an amino acid sequence set forth in SEQ ID NO:1 (1-84 PTH), and having the following characteristics: the N-terminal amino acid residue of the PTH antagonist starts at any position spanning position 2 through position 53 of the 1-84 PTH; the C-terminal amino acid residue of the PTH antagonist ends at any position spanning position 35 through position 84 of the 1-84 PTH; and the PTH antagonist has a minimal length of three amino acid residues. Frequently, a PTH antagonist is generically described as a contiguous portion of human PTH having an amino acid sequence set forth in SEQ ID NO:1 (1-84 PTH), and having the following characteristics: the N-terminal amino acid residue of the PTH antagonist starts at any position spanning position 2 through position 53 of the 1-84 PTH; the C-terminal amino acid residue of the PTH antagonist ends at position 84 of the 1-84 PTH; and the PTH antagonist has a minimal length of three amino acid residues.

In addition to the above described C-terminal PTH fragments (or PTH antagonists), calcitonin exhibits similar activity in the kidney with regard to the inhibition of the reabsorption of calcium. Similar to 7-84 PTH and other C-terminal PTH fragments, calcitonin decreases tubular reabsorption of calcium from the glomerulous filtrate. See P. A. Friedman & F. A. Gesek, *Physiol. Rev.* (1995) 75:429-71. Thus, the present disclosure recognizes that a reduction of serum calcium following administration (or otherwise increasing or increased in vivo concentrations) of calcitonin (and/or other PTH antagonists and C-terminal PTH fragments provided herein) would be accompanied by an increase in urinary calcium levels. Thus, the present disclosure recognizes the importance of monitoring calcitonin levels and/or levels of C-terminal PTH fragments, including and in addition to 7-84 PTH and/or NHERF1 expression or other factors, as an assessment for determining the risk of development of renal stones in a subject.

In a frequent embodiment, the risk of developing or having renal stones in a subject is determined by measuring the level of 7-84 PTH in the subject. Also frequently, the risk of developing or having renal stones in a subject is determined by measuring the level of calcitonin in the subject. In another frequent embodiment, the risk of developing or having renal stones is determined by measuring the level of 7-84 PTH, optionally together with measuring the level of calcitonin in the subject. In a less frequent embodiment, the risk of developing or having renal stones in a subject is determined by measuring the level of C-terminal PTH fragments other than or in addition to 7-84 PTH in the subject. Although these measured values may frequently be compared with corresponding standardized or control values or corresponding values obtained in normal individuals for the risk determination, such comparison is not mandatory. On occasion, the level of PTH antagonist and/or calcitonin is at a level that indicates that the subject is at risk for developing or having a renal stone.

As evidenced by the foregoing, calcium reabsorption and excretion within the kidney are affected by PTH agonists such as 1-84 PTH and PTH antagonists such as 7-84 PTH. Thus, it is often important to evaluate the levels of both of these components to determine whether calcium is being adequately reabsorbed in the kidney. A comparison of these components, such as a ratio or proportion is one means of comparing these concentrations. For example, a ratio of PTH agonist versus PTH antagonist may provide an indication of whether a subject is at risk for the development of renal stones. Other ratios are contemplated such as PTH antagonist versus PTH agonist, total PTH versus PTH agonist, total PTH versus PTH antagonist, PTH agonist versus total PTH, or PTH antagonist versus total PTH.

In the example of a ratio of PTH agonist versus PTH antagonist, a decreasing ratio over time will provide an indication that the subject may be at risk for the development of kidney stones. A ratio of 1-84 PTH versus PTH antagonist that is less than a reference standard will also provide an indication that a subject may be (or is) at risk for the development of renal stones. On occasion, when a measured ratio is compared with a reference standard ratio, a calculation or conversion will be necessary to meaningfully compare the two values.

In the example of a ratio of PTH antagonist versus total PTH, an increasing ratio over time will provide an indication that the subject may be (or is) at risk for the development of kidney stones. A ratio of PTH antagonist versus total PTH that is more than a reference standard will also provide an indication that a subject may be (or is) at risk for the development of renal stones.

Often, the measured level of a specific analyte is indicative of whether the subject is at an increased risk of developing or having a renal stone. Generally, if the measured analyte level is at (or above or below) a specific, often pre-designated, level the subject is at risk for developing or having a renal stone. Further, based on the measured level of the analyte, it is often determined that a ratio of the one or more analytes should be utilized to monitor, diagnose and/or guide treatment for renal stone disease. In this embodiment, the level of the analyte is utilized as a gate indicating when the use of a ratio-based evaluation of the sample would be appropriate or medically indicated. For example, often the level of an analyte may be present at a specific level (often a high or low level) that it provides an indication of the risk of a subject developing or having a renal stone, without resorting to a ratio-based analysis. As indicated herein, the analyte can be any one or more of a PTH antagonist, a PTH agonist, calcitonin, NHERF1 expression, and/or serum, blood or urinary calcium levels.

In the example of a ratio of PTH agonist versus total PTH, a decreasing ratio over time will provide an indication that the subject may be (or is) at risk for the development of kidney stones. A ratio of PTH agonist versus total PTH that is less than a reference standard will also provide an indication that a subject may be (or is) at risk for the development of renal stones.

In another frequent embodiment, the subject is evaluated for expression of NHERF1, optionally together with determining calcitonin levels, PTH antagonist levels and/or ratios of PTH components as set forth herein. Determination of NHERF1 expression in the subject may yield a lower overall risk of developing or having renal stones, even in the presence of increased PTH antagonist levels or low PTH agonist versus PTH antagonist ratios. Moreover, if there is a lack of NHERF1 expression in the subject, this subject may be determined to have a higher risk of developing or having renal stones, even in the presence of relatively lower PTH antagonist levels or relatively higher PTH agonist versus PTH antagonist ratios. On occasion, PTH component ratios and levels are interpreted in light of the presence, absence and/or level of functional NHERF1 protein expression. NHERF1 expression analysis may be coupled together with any other methods or kits discussed or contemplated herein, including but not limited to risk analysis and treatment monitoring.

A "reference standard" may be generated for any one or combination of variables or indices utilized to assess the risk of a subject developing or having renal stones. In one embodiment, a reference standard is generated by evaluating subjects for PTH antagonist levels or PTH level ratios (e.g., PTH agonist versus PTH antagonist) over time and following up with independent medical confirmation of renal stones via traditional methodologies. The reference standard will account for PTH antagonist levels or PTH level ratios in the subject prior to and at the time of confirmation of renal stones. Frequently, the standard will be generated based on one or more group of subjects having the same or similar family, medical or personal histories. On occasion, the standard will be generated based on one or more group of subjects having different family, medical or personal histories. Often the group will be selected from a particular patient population, for example, those with a family history of, or prior personal history of, stone formation. Also frequently, the group will be selected from a patient population having a specific medical disorder. On occasion, a random selection of subjects will be utilized to generate, elaborate on and/or verify a reference standard. A reference standard may be specifically or generally applicable. The reference standard will often be a selected numerical range of PTH antagonist levels or a range of selected PTH agonist and antagonist component ratios. The reference standard(s) are useful to measure and compare subsequent assays of subjects to determine their risk of developing or having renal stones. As one of skill in the art would understand, reference standards can be generated for any one or more analytes discussed herein, including but not limited to PTH, calcitonin, NHERF1 expression, and urinary, blood or serum calcium levels, among others.

In a frequent embodiment, the PTH antagonist level in a subject is compared with a normal "reference sample." The normal reference sample may be obtained from a normal subject or be comprised of a pool of samples from normal subjects. Frequently, the normal reference sample is a synthetically prepared PTH sample. Also frequently, the normal reference sample comprises PTH components obtained from one or more normal subjects. The normal reference sample frequently comprises known total PTH, PTH agonist and/or PTH antagonist levels within a normal range. Often the normal range of PTH agonist and PTH antagonist levels in the reference sample will be normal with regard to the general non-patient population as a whole. On occasion, the normal range of PTH agonist and PTH antagonist levels in the reference sample will be normal with regard to a specific patient population. The latter of these two is important for subjects that have PTH agonist and/or PTH antagonist levels that, although they may deviate from the normal population, may not be indicative of an increase in the risk of that subject developing or having a renal stone. As one of skill in the art would understand, normal reference samples can be prepared or utilized which contain known PTH component levels, calcitonin levels, urinary, blood or serum calcium levels, NHERF1 expression, and/or known levels of other analytes discussed or contemplated herein.

In one embodiment, the measured total PTH level, PTH agonist level, PTH antagonist level, or a ratio calculated therefrom are entered into an algorithm to evaluate the risk that the subject will develop or has renal stones. The algorithm is generated utilizing patient data and accounts for multiple variables. For example, the algorithm may include an assessment of one or more of: PTH antagonist levels, PTH agonist levels, total PTH levels, ratios of PTH components (e.g., total PTH, PTH agonist, PTH antagonist), urinary calcium levels, blood or serum calcium levels, scaffolding protein expression (e.g., NHERF1), medical history, family history, diet, among other variables specifically discussed or contemplated herein or otherwise known in the art. In general, the use of an algorithm provides an example mode of correlating one or more variables with the risk that a subject will develop or has a renal stone.

C. Symptoms, Risk Factors and Confirmation of Renal Stones

In general, when a subject becomes symptomatic for renal stones, one or more stones have already developed; such symptoms often include pain, infection, hematuria, fever, and/or nausea/vomiting. See, e.g., M. J. Stoller, *Urinary Stone Disease*, in SMITH'S GENERAL UROLOGY at 264-68.

A variety of risk factors are also known as being associated with in increased risk of developing renal stones. Such factors include crystalluria, socioeconomic factors, diet, occupation, climate, family history, medical history, and medications. See id. at 268-72. In an occasional embodiment, prior history or diagnosis of primary hyperparathyroidism is not utilized as a risk factor for developing renal stones.

In frequent embodiments, known risk factors and symptoms may be additionally evaluated or assessed in the determination of a subject's risk for the development of or having renal stones. Moreover, frequently such known risk factors and symptoms may be additionally evaluated or assessed in the confirmation of a subject's preliminary diagnosis of the presence of renal stones.

With further regard to the confirmation of the diagnosis of renal stones or evaluation of the risk of a subject for the development of renal stones, physical examination and/or radiological examination may be utilized. See id.

D. Therapy Considerations

Several options exist for the treatment of renal stones after diagnosis or recognition. Frequently, however, most calculi pass from the bladder and/or urethral passage without intervention. The location, size and shape of the calculi, together with often associated urethral damage, affect the probability of spontaneous passage. See M. J. Stoller, *Urinary Stone Disease*, in SMITH'S GENERAL UROLOGY at 273-4. In the event that the stone does not pass spontaneously, intervention or associated therapies may be recommended. A broad array of therapies are available, ranging in their degree of invasiveness.

Dissolution agents such as oral or intravenous alkalinizing or acidification agents may be used to dissolve renal stones. Examples of dissolution agents include, for example, sodium bicarbonate, potassium bicarbonate, potassium citrate, sodium lactate, tromethamine and tromethamine-E, D-penicillamine, N-acetylcysteine, alpha-mercaptopropionylglycine, Suby's G solution, or hemiacidrin. Other examples of dissolution agents are available and known in the art and are contemplated herein.

On occasion, a subject may require immediate relief from a renal stone that poses significant health related risks due to obstruction, optionally coupled with infection. In such cases drainage may be therapeutically indicated utilizing a ureteral stent or a nephrostomy tube.

Other therapies to break up, or otherwise remove, renal stones include extracorporeal shock lithotripsy, ureteroscopic stone extraction, percutaneous nephrolithotomy, open stone surgery, pyelolithotomy, anatrophic nephrolithotomy, radial nephrotomy, ureterolithotomy, partial nephrectomy, ileal ureter substitution, or autotransplantation with pyelocystostomy.

Other therapies are available and known in the art and may incorporate various diet-modification or herbal therapies, nutritional supplementation, and/or pharmaceutically-based and/or invasive therapies. Although such therapies may not be listed specifically herein, they are contemplated and incorporated in the present disclosure by way of their general knowledge in the art.

Frequently, any one or more of the above therapies are instituted after evaluation of the risk of a subject for the development of renal stones in accordance with the methods provided herein. These methods encompass the evaluation for the reoccurrence of renal stones in a subject. Less invasive therapies such as diet modification, nutritional supplementation and/or pharmaceutical administration are frequently utilized when a subject is determined to be at risk for developing renal stones. Generally, however, in the event renal stone development is confirmed in the subject, therapies in addition to or in lieu of these less invasive therapies may be instituted or continued in the subject. In less occasional embodiments, therapy is decreased or stopped after evaluating the risk of a subject for developing renal stones in accordance with the methods provided herein based on the determined risk.

In a frequent embodiment, methods are contemplated that monitor the effectiveness of one or more therapeutic options. Such methods often comprise measurement of 7-84 PTH levels, C-terminal PTH fragment levels in addition to 7-84 PTH, NHERF1 expression, calcitonin levels, total PTH levels, whole PTH levels, N-terminal PTH fragment levels, or calculation of ratios generated from the measurement and comparison of one or more of these parameters. In addition or alternatively, therapeutic efficacy may be monitored via monitoring urine and/or serum and/or blood calcium levels. Moreover, other known risk factors for the development of renal stones may be measured and monitored, optionally together with these factors, for monitoring treatment.

E. Parathyroid Hormone Antagonists

In one aspect, the present disclosure contemplates PTH antagonists comprising a contiguous portion of human PTH having an amino acid sequence set forth in SEQ ID NO:1 (1-84 PTH), or a nucleic acid encoding said portion of human PTH, which PTH antagonist has the following characteristics: a) the N-terminal amino acid residue of the PTH antagonist starts at any position spanning position 2 through position 53 of said 1-84 PTH; b) the C-terminal amino acid residue of the PTH antagonist ends at any position spanning position 35 through position 84 of the 1-84 PTH; and c) said PTH antagonist has a minimal length of three amino acid residues. Frequently the C-terminal position ends at about position 84 of the 1-84 PTH, such as at about position 74, 75, 76, 77, 78, 79, 80, 81, 82, 83 or 84 of the 1-84 PTH.

The N-terminal amino acid residue of the PTH antagonist can start at any position spanning position 2 through position 53 of said 1-84 PTH. For example, the N-terminal amino acid residue of the PTH antagonist can start at position 2, 3, 4, 5, 6, 7, 8, 9, 10 . . . 30, 31, 32, 33, 34 . . . 50, 51, 52, 53 of 1-84 PTH. The C-terminal amino acid residue of said PTH antagonist can end at or about position 84 of said 1-84 PTH.

In a specific embodiment, the PTH antagonist is a protein or a peptide, or a nucleic acid encoding said protein or peptide, selected from the group consisting of 2-84 PTH (SEQ ID NO:2), 3-84 PTH (SEQ ID NO:3), 4-84 PTH (SEQ ID NO:4), 5-84 PTH (SEQ ID NO:5), 6-84 PTH (SEQ ID NO:6), 7-84 PTH (SEQ ID NO:7), 8-84 PTH (SEQ ID NO:8), 9-84 PTH (SEQ ID NO:9), 10-84 PTH (SEQ ID NO:10), 11-84 PTH (SEQ ID NO:11), 12-84 PTH (SEQ ID NO:12), 13-84 PTH (SEQ ID NO:13), 14-84 PTH (SEQ ID NO:14), 15-84 PTH (SEQ ID NO:15), 16-84 PTH (SEQ ID NO:16), 17-84 PTH (SEQ ID NO:17), 18-84 PTH (SEQ ID NO:18), 19-84 PTH (SEQ ID NO:19), 20-84 PTH (SEQ ID NO:20), 21-84 PTH (SEQ ID NO:21), 22-84 PTH (SEQ ID NO:22), 23-84 PTH (SEQ ID NO:23), 24-84 PTH (SEQ ID NO:24), 25-84 PTH (SEQ ID NO:25), 26-84 PTH (SEQ ID NO:26), 27-84 PTH (SEQ ID NO:27), 28-84 PTH (SEQ ID NO:28), 29-84 PTH (SEQ ID NO:29), 30-84 PTH (SEQ ID NO:30), 31-84 PTH (SEQ ID NO:31), 32-84 PTH (SEQ ID NO:32), 33-84 PTH (SEQ ID NO:33), 34-84 PTH (SEQ ID NO:34), 35-84 PTH (SEQ ID NO:35), 36-84 PTH (SEQ ID NO:36), 37-84 PTH (SEQ ID NO:37), 38-84 PTH (SEQ ID NO:38), 39-84 PTH (SEQ ID NO:39), 40-84 PTH (SEQ ID NO:40), 41-84 PTH (SEQ ID NO:41), 42-84 PTH (SEQ ID NO:42), 43-84 PTH (SEQ ID NO:43), 44-84 PTH (SEQ ID NO:44), 45-84 PTH (SEQ ID NO:45), 46-84 PTH (SEQ ID NO:46), 47-84 PTH (SEQ ID NO:47), 48-84 PTH (SEQ ID NO:48), 49-84 PTH (SEQ ID NO:49), 50-84 PTH (SEQ ID NO:50), 51-84 PTH (SEQ ID NO:51), 52-84 PTH (SEQ ID NO:52), 53-84 PTH (SEQ ID NO:53). As indicated, although the C-terminal position of the PTH antagonist frequently ends at position 84, it is not required.

In another embodiment, the PTH antagonist comprises a protein or peptide, or is encoded by a nucleotide, that is about 90% identical to the sequence set forth in a PTH antagonist described above. Often the PTH antagonist is about or more than 90% identical to the sequence set forth in a PTH antagonist described above. More frequently, the PTH antagonist is about 91%, 92%, 93, 94%, 95%, 96%, 97%, 98%, or about 99% identical to the sequence set forth in a PTH antagonist described above.

The PTH antagonist can have any suitable length provided that it maintains its antagonizing activity. For example, the PTH antagonist can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid residues.

The PTH antagonist can further comprise an amino acid residue substitution or modification that enhances or does not decrease its antagonist activity, or an amino acid residue substitution or modification that stabilizes the PTH antagonist. Often, when the PTH antagonist comprises a polypeptide sequence altered from that set forth above, it is due to natural polymorphisms and generally will not affect its biological activity. For example, the PTH antagonist can further comprise the following amino acid residue substitution or modification: $His_{25}$, $His_{26}$, $Leu_{27}$, (U.S. Pat. No. 5,382,658); $Tyr_{34}$, $D-Trp_{12}$, $Nle_{8,18}$, desamino($Nle_{8,18}$), $Lys_{13}$ modified in the epsilon-amino acid group by N,N-diisobutyl or 3-phenyl-propanoyl (U.S. Pat. No. 5,093,233); $Gly_{12}$ substituted by D-Trp, L-Trp, L- or D-α- or β-naphthylalanine, or D- or L-α-MeTrp (U.S. Pat. No. 4,968,669); the amino acid residue at positions 7, 11, 23, 24, 27, 28, or 31 being cyclohexylalanine, the amino acid residue at position 3, 16, 17, 18, 19, or 34 being α-aminoisobutyric acid, the amino acid residue at position 1 being α,β-diaminopropionic acid, the amino acid residue at position 27 being homoarginine, the amino acid residue at position 31 being norleucine (U.S. Pat. No. 5,723,577); each of $Arg_{25}$, $Lys_{26}$, $Lys_{27}$ being substituted with Ala, Asn, Asp, Cys, Gln, Glu, Gly, His, Ile, Leu, Met, Phe, Pro, Ser, Thr, Trp, Tyr or Val (U.S. Pat. No. 5,317,010); and a combination thereof.

F. Parathyroid Hormone Agonists

In one aspect, the present disclosure contemplates a PTH agonist comprising a contiguous portion of human PTH having an amino acid sequence set forth in SEQ ID NO:1 (1-84 PTH), and the PTH agonist has the following characteristics: a) the N-terminal amino acid residue of the PTH agonist starts at position 1 of the 1-84 PTH; and b) the C-terminal amino acid residue of the PTH agonist ends at any position spanning position 34 through position 84 of the 1-84 PTH.

Without being bound by theory, the N-terminal amino acid residue of the PTH agonist generally starts at position 1 of said 1-84 PTH. For example, the N-terminal amino acid residue of the PTH agonist can start at position 1 of the 1-84 PTH. The C-terminal amino acid residue of said PTH agonist can end at any position spanning position 34 through position 84 of said 1-84 PTH. For example, the C-terminal amino acid residue of the PTH agonist can end at position 84 of the 1-84 PTH.

In another embodiment, the PTH agonist comprises a protein or peptide, or is encoded by a nucleotide, that is about 90% identical to the sequence set forth in a PTH agonist described above. Often the PTH agonist is more than 90% identical to the sequence set forth in a PTH agonist described above. More frequently, the PTH agonist is about 91%, 92%, 93%, 94%, 95%, 96%, 97%, 98%, or about 99% identical to the sequence set forth in a PTH agonist described above.

The PTH agonist can have any suitable length provided that it maintains its agonizing activity. For example, the PTH agonist can have a length of 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid residues.

PTH agonists may comprise whole PTH, for example, see the peptides in U.S. Pat. Nos. 5,496,801, 5,208,041 or 4,086,196. Suitable PTH agonists may be derived from a variety of mammal species, for example bovine 1-35 and porcine 1-36 PTH peptide fragments (U.S. Pat. No. 5,783,558). The PTH agonist can further comprise an amino acid residue substitution or modification that enhances or does not decrease its agonist activity, or an amino acid residue substitution or modification that stabilizes the PTH agonist (see e.g., U.S. Pat. No. 5,382,658 (including $His_{25}$, $His_{26}$, and $Leu_{27}$ modifications)). PTH agonists, therefore, may comprise peptides which are structural analogs or fragments of a naturally occurring PTH (see e.g., U.S. Pat. No. 5,434,246 (including substitutions at the PTH 3, 14, 15, 16, 17, 25, 26, 27 or 34 amino acid positions); U.S. Pat. No. 4,656,250 (including PTH analogs with substitutions at the 8, 18 and 34 positions)). Synthetic polypeptide analogs of PTH, parathyroid hormone related peptide (PTHrp), and of the physiologically active truncated homologs and analogs of PTH and PTHrp, in which amino acid residues (22-31) form an amphipathic α-helix, said residues (22-31) selected from hydrophilic amino acids (Haa) and lipophilic amino acids (Laa) ordered in the sequence: $Haa(Laa\ Laa\ Haa\ Haa)_2\ Laa$ and their pharmaceutically acceptable salts. See U.S. Pat. Nos. 5,807,823; 5,840,831; 5,798,225; 5,695,955; and 5,589,452. Moreover, PTH agonists may also include synthetic peptides, i.e., parathyroid hormone-like protein (PLP), or naturally occurring peptides such as (PTH)-like hypercalcemic factor (hHCF), parathyroid-related protein (PTHrP), or parathyroid hormone-like adenylate cyclase-stimulating proteins (hACSPs). See, e.g., Yates, A J, et al., *J. Clin. Invest.* (1988) 81(3):932-8; Nissenson R A, et al., *J. Biol. Chem.* (1988) 263(26):12866-71; Thompson D D, et al., *Proc. Nat'l Acad. Sci.* (1988) 85(15): 5673-7; and Stewart, A F, et al., *J. Clin. Invest.* (1988) 81(2): 596-600. For example, the PTH agonist can further comprise the following amino acid residue substitution or modification of PTH, PLP, or PTHrP: each of $Ser_3$, $Gln_6$, $His_9$ being substituted with Ala, Arg, Asn, Asp, Cys, Gln, Glu, Gly, His, Ile, Leu, Lys, Met, Phe, Pro, Ser, Thr, Trp, Tyr or Val (U.S. Pat. No. 5,849,695). Other PTH and PTHrP agonists contemplated by the present disclosure may also include human PTH $(hPTH)_{1-34}NH_2$, $hPTH_{1-38}\ NH_2$, $hPTH_{1-44}\ NH_2$, $hPTH_{1-68}\ NH_2$, $[Nle^{8,18}, Tyr^{34}]bPTH_{1-34}NH_2$, $bPTH_{1-34}NH_2$, $[Nle^{8,18}, Tyr^{34}]bPTH_{1-34}$, $[Nle^{8,18}, Phe^{22}, Tyr^{34}]bPTH_{1-34}\ NH_2$, $[Nle^{8,18}, Arg^{19}, Tyr^{34}]bPTH_{1-34}\ NH_2$, $[Nle^{8,18}, Arg^{21}, Tyr^{34}]bPTH_{1-34}\ NH_2$, or $[Nle^{8,18}, Arg^{19,21}, Tyr^{34}]bPTH_{1-34}\ NH_2$. The symbol $NH_2$ denotes amidation of the carboxyl group (—CO.OH) of the C-terminal amino acid to form —$CO.NH_2$. See U.S. Pat. No. 5,747,456.

G. Kits

In a frequent embodiment, a kit is provided for testing for PTH agonist and/or PTH antagonist levels in a subject, which kit comprises, in a container, means for determining the level of a PTH antagonist in a sample obtained from a subject; and means for evaluating the level of the PTH antagonist and determining the risk of the subject for developing renal calcium calculi. Frequently the kit further comprises means for determining the level of a PTH agonist in the sample, and means for determining the risk of the subject for developing renal calcium calculi based on the PTH agonist and PTH antagonist levels. Also frequently, the kit further comprises means for determining the level of a PTH agonist and total PTH in the sample, and means for determining the risk of the subject for developing renal calcium calculi based on the PTH agonist level, the PTH antagonist level, the total PTH level and/or a combination thereof.

The invention also provides for kits for carrying out the methods of the invention. Such kits comprise in one or more containers a means for determining and/or monitoring the level of parathyroid hormone (PTH) agonist and/or PTH antagonist in a subject alone or in combination with other agents. Examples of means for determining and monitoring PTH agonist and antagonist levels in a patent comprise a variety of PTH assays described herein and known in the art.

In one embodiment, the kit of the present disclosure contains means for measuring and/or comparing any one or more of a variety of analytes discussed and contemplated herein. For example, means for evaluating analytes such as PTH agonist and antagonist levels, calcitonin levels, serum or blood calcium levels, urinary calcium levels, NHERF1 expression, among other analytes.

In one aspect, a kit of the invention further comprises a needle or syringe as a means for administering a therapeutic to a patient, preferably packaged in sterile form, for injecting the composition, and/or a packaged alcohol pad. Instructions are optionally included for administration of composition by a physician or by the patient.

Other features and advantages of the invention will be apparent from the following description.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

EXAMPLES

Example 1

A group of subjects are selected based on their propensity for forming renal stones. A second comparable group of subjects are selected based on their lack of propensity for forming renal stones. The propensity for forming stones accounts for one or more of a variety of factors including genetic factors, diet, history of stone formation, medical history, among other factors. Each subject may be individually selected and evaluated over time.

Blood or serum samples are obtained from each subject and are evaluated for 1-84 PTH, 7-84 PTH and/or total PTH concentrations. Optionally, samples are obtained and evaluated for 1-84 PTH, 7-84 PTH and/or total PTH concentrations at intervals over time.

Concurrent with or within a brief period of time of the formation of renal stones in one or more subjects, another sample is obtained from the subjects having renal stones, and optionally samples are obtained from each member of each group or selected members of any particular group of subjects. The samples are again evaluated for 1-84 PTH, 7-84 PTH and/or total PTH concentrations.

The 7-84 PTH level, the ratio of 1-84 PTH versus 7-84 PTH, the ratio of total PTH versus 7-84 PTH, and/or the ratio of total PTH versus 1-84 PTH of each subject are compared with the corresponding indices in each subject generated from samples obtained at an earlier time, and prior to the formation of a renal stone.

If evaluated, the level of 7-84 PTH prior to and at the time of stone formation or presence are compared. If evaluated, the ratio of 1-84 PTH versus 7-84 PTH prior to and at the time of stone formation or presence are compared. If evaluated, the ratio of total PTH versus 7-84 PTH prior to and at the time of stone formation or presence are compared. If evaluated, the ratio of total PTH versus 1-84 PTH prior to and at the time of stone formation or presence are compared.

In another example, the serum and/or urine calcium levels are evaluated in each of the above subjects at the same time that the 1-84 PTH, 7-84 PTH and/or total PTH concentrations are evaluated. The serum and/or urine calcium levels prior to and at the time of stone formation or presence are compared. The serum and/or urine calcium levels are optionally evaluated while taking into account the 1-84 PTH, 7-84 PTH and/or total PTH concentration comparisons set out above.

In yet another example, NHERF1 expression is evaluated in each of the above subjects at the same time that the 1-84 PTH, 7-84 PTH and/or total PTH concentrations are evaluated. The NHERF1 expression levels determined prior to and at the time of stone formation or presence are compared. The NHERF1 expression levels are optionally evaluated while taking into account the 1-84 PTH, 7-84 PTH and/or total PTH concentration comparisons set out above.

In another example, a set of subjects is comprised of subjects with a history of stone formation and are undergoing therapy to decrease the risk for reoccurrence of renal stones.

Data generated from the above experiments are utilized to determine the risk of a subject for developing renal calcium calculi, or to monitor, modify and/or evaluate treatment methodologies intended to reduce the risk for reoccurrence of renal stones.

Example 2

Although not intended to provide a complete list of the presently contemplated alternative embodiments, the following set forth a series of embodiments contemplated in the present disclosure. As indicated above, these exemplifications, while illustrating certain specific aspects of the invention, do not portray the limitations or circumscribe the scope of the disclosed invention.

The above examples are included for illustrative purposes only and are not intended to limit the scope of the invention. Many variations to those described above are possible.

Citation of the above publications or documents is not intended as an admission that any of the foregoing is pertinent prior art, nor does it constitute any admission as to the contents or date of these publications or documents.

The invention claimed is:

1. A method for determining the risk of a subject for developing renal calcium calculi comprising:
   a) determining the level of parathyroid hormone (PTH) agonist and the level of PTH antagonist in a sample obtained from a subject;
   b) comparing the level of PTH agonist and PTH antagonist in the sample in a ratio; and
   c) determining the risk for developing renal calcium calculi in the subject based on the ratio;
   wherein the PTH agonist is a peptide having an amino acid sequence of human 1-84 PTH (SEQ ID NO:1);
   and the PTH antagonist is-7-84 PTH (SEQ ID NO:7).

2. The method of claim 1, wherein the sample is a urine, blood or serum sample.

3. The method of claim 1 further comprising comparing the ratio to a reference standard, or to a ratio determined with a normal reference sample to determine the risk for developing renal calcium calculi in the subject.

4. The method of claim 1 further comprising determining a serum calcium level, a urinary calcium level or combination thereof in the subject.

5. The method of claim 4, wherein the risk for developing renal calcium calculi in the subject is determined based on the ratio, the serum calcium level, the urinary calcium level or a combination thereof.

6. The method of claim 1, wherein steps (a-c) are repeated for the subject at pre-designated time intervals.

7. The method of claim 6, wherein the ratio of a later interval is compared with: (1) a ratio in the subject obtained at an earlier interval; or (2) an average of ratios calculated from ratios obtained at two or more earlier intervals.

8. The method of claim 6, wherein if the ratio of PTH agonist versus PTH antagonist of a later interval is more than the ratio of PTH agonist versus PTH antagonist at a earlier interval or if there is a trend of increasing ratios of PTH agonist versus PTH antagonist over the course of one or more intervals, the subject is considered to be at risk for developing or having renal stones.

9. The method of claim 6 wherein the ratio is compared with a ratio obtained at an earlier interval.

10. The method of claim 1, wherein the risk determination is utilized to monitor and/or guide treatment for renal calculi.

11. The method of claim 10, wherein the determination of a higher or increasing risk indicates that treatment for renal calculi should be commenced, continued or modified, and the determination of a lower or decreasing risk indicates that treatment for renal stones should end, decrease or be modified.

12. The method of claim 1, further comprising determining the total PTH level in the sample and comparing the level of PTH agonist, PTH antagonist and/or the total PTH level in a ratio, and determining the risk for developing renal calcium calculi in the subject based on the ratio.

13. The method of claim 1, wherein the subject is a mammal.

14. The method of claim 13, wherein the mammal is a human.

* * * * *

SEQUENCE LISTING

```
<160> NUMBER OF SEQ ID NOS: 53

<210> SEQ ID NO 1
<211> LENGTH: 84
<212> TYPE: PRT
<213> ORGANISM: Homo sapiens
<220> FEATURE:
<221> NAME/KEY: PEPTIDE
<222> LOCATION: (1)...(84)
<223> OTHER INFORMATION: human parathyroid hormone peptide fragment

<400> SEQUENCE: 1

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45
```

-continued

```
Gln Arg Pro Arg Lys Lys Glu Asp Asn Val Leu Val Glu Ser His Glu
     50                  55                  60

Lys Ser Leu Gly Glu Ala Asp Lys Ala Asp Val Asn Val Leu Thr Lys
 65                  70                  75                  80

Ala Lys Ser Gln

<210> SEQ ID NO 2
<211> LENGTH: 83
<212> TYPE: PRT
<213> ORGANISM: Homo sapiens
<220> FEATURE:
<221> NAME/KEY: PEPTIDE
<222> LOCATION: (1)...(83)
<223> OTHER INFORMATION: human parathyroid hormone peptide fragment

<400> SEQUENCE: 2

Val Ser Glu Ile Gln Leu Met His Asn Leu Gly Lys His Leu Asn Ser
 1               5                  10                  15

Met Glu Arg Val Glu Trp Leu Arg Lys Lys Leu Gln Asp Val His Asn
             20                  25                  30

Phe Val Ala Leu Gly Ala Pro Leu Ala Pro Arg Asp Ala Gly Ser Gln
         35                  40                  45

Arg Pro Arg Lys Lys Glu Asp Asn Val Leu Val Glu Ser His Glu Lys
     50                  55                  60

Ser Leu Gly Glu Ala Asp Lys Ala Asp Val Asn Val Leu Thr Lys Ala
 65                  70                  75                  80

Lys Ser Gln

<210> SEQ ID NO 3
<211> LENGTH: 82
<212> TYPE: PRT
<213> ORGANISM: Homo sapiens
<220> FEATURE:
<221> NAME/KEY: PEPTIDE
<222> LOCATION: (1)...(82)
<223> OTHER INFORMATION: human parathyroid hormone peptide fragment

<400> SEQUENCE: 3

Ser Glu Ile Gln Leu Met His Asn Leu Gly Lys His Leu Asn Ser Met
 1               5                  10                  15

Glu Arg Val Glu Trp Leu Arg Lys Lys Leu Gln Asp Val His Asn Phe
             20                  25                  30

Val Ala Leu Gly Ala Pro Leu Ala Pro Arg Asp Ala Gly Ser Gln Arg
         35                  40                  45

Pro Arg Lys Lys Glu Asp Asn Val Leu Val Glu Ser His Glu Lys Ser
     50                  55                  60

Leu Gly Glu Ala Asp Lys Ala Asp Val Asn Val Leu Thr Lys Ala Lys
 65                  70                  75                  80

Ser Gln

<210> SEQ ID NO 4
<211> LENGTH: 81
<212> TYPE: PRT
<213> ORGANISM: Homo sapiens
<220> FEATURE:
<221> NAME/KEY: PEPTIDE
<222> LOCATION: (1)...(81)
<223> OTHER INFORMATION: human parathyroid hormone peptide fragment
```

<400> SEQUENCE: 4

```
Glu Ile Gln Leu Met His Asn Leu Gly Lys His Leu Asn Ser Met Glu
  1               5                  10                  15

Arg Val Glu Trp Leu Arg Lys Lys Leu Gln Asp Val His Asn Phe Val
                 20                  25                  30

Ala Leu Gly Ala Pro Leu Ala Pro Arg Asp Ala Gly Ser Gln Arg Pro
             35                  40                  45

Arg Lys Lys Glu Asp Asn Val Leu Val Glu Ser His Glu Lys Ser Leu
 50                  55                  60

Gly Glu Ala Asp Lys Ala Asp Val Asn Val Leu Thr Lys Ala Lys Ser
 65                  70                  75                  80

Gln
```

<210> SEQ ID NO 5
<211> LENGTH: 80
<212> TYPE: PRT
<213> ORGANISM: Homo sapiens
<220> FEATURE:
<221> NAME/KEY: PEPTIDE
<222> LOCATION: (1)...(80)
<223> OTHER INFORMATION: human parathyroid hormone peptide fragment

<400> SEQUENCE: 5

```
Ile Gln Leu Met His Asn Leu Gly Lys His Leu Asn Ser Met Glu Arg
  1               5                  10                  15

Val Glu Trp Leu Arg Lys Lys Leu Gln Asp Val His Asn Phe Val Ala
                 20                  25                  30

Leu Gly Ala Pro Leu Ala Pro Arg Asp Ala Gly Ser Gln Arg Pro Arg
             35                  40                  45

Lys Lys Glu Asp Asn Val Leu Val Glu Ser His Glu Lys Ser Leu Gly
 50                  55                  60

Glu Ala Asp Lys Ala Asp Val Asn Val Leu Thr Lys Ala Lys Ser Gln
 65                  70                  75                  80
```

<210> SEQ ID NO 6
<211> LENGTH: 79
<212> TYPE: PRT
<213> ORGANISM: Homo sapiens
<220> FEATURE:
<221> NAME/KEY: PEPTIDE
<222> LOCATION: (1)...(79)
<223> OTHER INFORMATION: human parathyroid hormone peptide fragment

<400> SEQUENCE: 6

```
Gln Leu Met His Asn Leu Gly Lys His Leu Asn Ser Met Glu Arg Val
  1               5                  10                  15

Glu Trp Leu Arg Lys Lys Leu Gln Asp Val His Asn Phe Val Ala Leu
                 20                  25                  30

Gly Ala Pro Leu Ala Pro Arg Asp Ala Gly Ser Gln Arg Pro Arg Lys
             35                  40                  45

Lys Glu Asp Asn Val Leu Val Glu Ser His Glu Lys Ser Leu Gly Glu
 50                  55                  60

Ala Asp Lys Ala Asp Val Asn Val Leu Thr Lys Ala Lys Ser Gln
 65                  70                  75
```

<210> SEQ ID NO 7
<211> LENGTH: 78
<212> TYPE: PRT
<213> ORGANISM: Homo sapiens

```
<220> FEATURE:
<221> NAME/KEY: PEPTIDE
<222> LOCATION: (1)...(78)
<223> OTHER INFORMATION: human parathyroid hormone peptide fragment

<400> SEQUENCE: 7

Leu Met His Asn Leu Gly Lys His Leu Asn Ser Met Glu Arg Val Glu
 1               5                  10                  15

Trp Leu Arg Lys Lys Leu Gln Asp Val His Asn Phe Val Ala Leu Gly
                20                  25                  30

Ala Pro Leu Ala Pro Arg Asp Ala Gly Ser Gln Arg Pro Arg Lys Lys
            35                  40                  45

Glu Asp Asn Val Leu Val Glu Ser His Glu Lys Ser Leu Gly Glu Ala
 50                  55                  60

Asp Lys Ala Asp Val Asn Val Leu Thr Lys Ala Lys Ser Gln
 65                  70                  75

<210> SEQ ID NO 8
<211> LENGTH: 77
<212> TYPE: PRT
<213> ORGANISM: Homo sapiens
<220> FEATURE:
<221> NAME/KEY: PEPTIDE
<222> LOCATION: (1)...(77)
<223> OTHER INFORMATION: human parathyroid hormone peptide fragment

<400> SEQUENCE: 8

Met His Asn Leu Gly Lys His Leu Asn Ser Met Glu Arg Val Glu Trp
 1               5                  10                  15

Leu Arg Lys Lys Leu Gln Asp Val His Asn Phe Val Ala Leu Gly Ala
                20                  25                  30

Pro Leu Ala Pro Arg Asp Ala Gly Ser Gln Arg Pro Arg Lys Lys Glu
            35                  40                  45

Asp Asn Val Leu Val Glu Ser His Glu Lys Ser Leu Gly Glu Ala Asp
 50                  55                  60

Lys Ala Asp Val Asn Val Leu Thr Lys Ala Lys Ser Gln
 65                  70                  75

<210> SEQ ID NO 9
<211> LENGTH: 76
<212> TYPE: PRT
<213> ORGANISM: Homo sapiens
<220> FEATURE:
<221> NAME/KEY: PEPTIDE
<222> LOCATION: (1)...(76)
<223> OTHER INFORMATION: human parathyroid hormone peptide fragment

<400> SEQUENCE: 9

His Asn Leu Gly Lys His Leu Asn Ser Met Glu Arg Val Glu Trp Leu
 1               5                  10                  15

Arg Lys Lys Leu Gln Asp Val His Asn Phe Val Ala Leu Gly Ala Pro
                20                  25                  30

Leu Ala Pro Arg Asp Ala Gly Ser Gln Arg Pro Arg Lys Lys Glu Asp
            35                  40                  45

Asn Val Leu Val Glu Ser His Glu Lys Ser Leu Gly Glu Ala Asp Lys
 50                  55                  60

Ala Asp Val Asn Val Leu Thr Lys Ala Lys Ser Gln
 65                  70                  75
```

```
<210> SEQ ID NO 10
<211> LENGTH: 75
<212> TYPE: PRT
<213> ORGANISM: Homo sapiens
<220> FEATURE:
<221> NAME/KEY: PEPTIDE
<222> LOCATION: (1)...(75)
<223> OTHER INFORMATION: human parathyroid hormone peptide fragment

<400> SEQUENCE: 10

Asn Leu Gly Lys His Leu Asn Ser Met Glu Arg Val Glu Trp Leu Arg
 1               5                  10                  15

Lys Lys Leu Gln Asp Val His Asn Phe Val Ala Leu Gly Ala Pro Leu
            20                  25                  30

Ala Pro Arg Asp Ala Gly Ser Gln Arg Pro Arg Lys Lys Glu Asp Asn
        35                  40                  45

Val Leu Val Glu Ser His Glu Lys Ser Leu Gly Glu Ala Asp Lys Ala
50                  55                  60

Asp Val Asn Val Leu Thr Lys Ala Lys Ser Gln
65                  70                  75

<210> SEQ ID NO 11
<211> LENGTH: 74
<212> TYPE: PRT
<213> ORGANISM: Homo sapiens
<220> FEATURE:
<221> NAME/KEY: PEPTIDE
<222> LOCATION: (1)...(74)
<223> OTHER INFORMATION: human parathyroid hormone peptide fragment

<400> SEQUENCE: 11

Leu Gly Lys His Leu Asn Ser Met Glu Arg Val Glu Trp Leu Arg Lys
 1               5                  10                  15

Lys Leu Gln Asp Val His Asn Phe Val Ala Leu Gly Ala Pro Leu Ala
            20                  25                  30

Pro Arg Asp Ala Gly Ser Gln Arg Pro Arg Lys Lys Glu Asp Asn Val
        35                  40                  45

Leu Val Glu Ser His Glu Lys Ser Leu Gly Glu Ala Asp Lys Ala Asp
50                  55                  60

Val Asn Val Leu Thr Lys Ala Lys Ser Gln
65                  70

<210> SEQ ID NO 12
<211> LENGTH: 73
<212> TYPE: PRT
<213> ORGANISM: Homo sapiens
<220> FEATURE:
<221> NAME/KEY: PEPTIDE
<222> LOCATION: (1)...(73)
<223> OTHER INFORMATION: human parathyroid hormone peptide fragment

<400> SEQUENCE: 12

Gly Lys His Leu Asn Ser Met Glu Arg Val Glu Trp Leu Arg Lys Lys
 1               5                  10                  15

Leu Gln Asp Val His Asn Phe Val Ala Leu Gly Ala Pro Leu Ala Pro
            20                  25                  30

Arg Asp Ala Gly Ser Gln Arg Pro Arg Lys Lys Glu Asp Asn Val Leu
        35                  40                  45

Val Glu Ser His Glu Lys Ser Leu Gly Glu Ala Asp Lys Ala Asp Val
50                  55                  60

Asn Val Leu Thr Lys Ala Lys Ser Gln
65                  70
```

<210> SEQ ID NO 13
<211> LENGTH: 72
<212> TYPE: PRT
<213> ORGANISM: Homo sapiens
<220> FEATURE:
<221> NAME/KEY: PEPTIDE
<222> LOCATION: (1)...(72)
<223> OTHER INFORMATION: human parathyroid hormone peptide fragment

<400> SEQUENCE: 13

```
Lys His Leu Asn Ser Met Glu Arg Val Glu Trp Leu Arg Lys Lys Leu
 1               5                  10                  15
Gln Asp Val His Asn Phe Val Ala Leu Gly Ala Pro Leu Ala Pro Arg
            20                  25                  30
Asp Ala Gly Ser Gln Arg Pro Arg Lys Lys Glu Asp Asn Val Leu Val
        35                  40                  45
Glu Ser His Glu Lys Ser Leu Gly Glu Ala Asp Lys Ala Asp Val Asn
    50                  55                  60
Val Leu Thr Lys Ala Lys Ser Gln
65                  70
```

<210> SEQ ID NO 14
<211> LENGTH: 71
<212> TYPE: PRT
<213> ORGANISM: Homo sapiens
<220> FEATURE:
<221> NAME/KEY: PEPTIDE
<222> LOCATION: (1)...(71)
<223> OTHER INFORMATION: human parathyroid hormone peptide fragment

<400> SEQUENCE: 14

```
His Leu Asn Ser Met Glu Arg Val Glu Trp Leu Arg Lys Lys Leu Gln
 1               5                  10                  15
Asp Val His Asn Phe Val Ala Leu Gly Ala Pro Leu Ala Pro Arg Asp
            20                  25                  30
Ala Gly Ser Gln Arg Pro Arg Lys Lys Glu Asp Asn Val Leu Val Glu
        35                  40                  45
Ser His Glu Lys Ser Leu Gly Glu Ala Asp Lys Ala Asp Val Asn Val
    50                  55                  60
Leu Thr Lys Ala Lys Ser Gln
65                  70
```

<210> SEQ ID NO 15
<211> LENGTH: 70
<212> TYPE: PRT
<213> ORGANISM: Homo sapiens
<220> FEATURE:
<221> NAME/KEY: PEPTIDE
<222> LOCATION: (1)...(70)
<223> OTHER INFORMATION: human parathyroid hormone peptide fragment

<400> SEQUENCE: 15

```
Leu Asn Ser Met Glu Arg Val Glu Trp Leu Arg Lys Lys Leu Gln Asp
 1               5                  10                  15
Val His Asn Phe Val Ala Leu Gly Ala Pro Leu Ala Pro Arg Asp Ala
            20                  25                  30
Gly Ser Gln Arg Pro Arg Lys Lys Glu Asp Asn Val Leu Val Glu Ser
        35                  40                  45
His Glu Lys Ser Leu Gly Glu Ala Asp Lys Ala Asp Val Asn Val Leu
    50                  55                  60
Thr Lys Ala Lys Ser Gln
65                  70
```

```
<210> SEQ ID NO 16
<211> LENGTH: 69
<212> TYPE: PRT
<213> ORGANISM: Homo sapiens
<220> FEATURE:
<221> NAME/KEY: PEPTIDE
<222> LOCATION: (1)...(69)
<223> OTHER INFORMATION: human parathyroid hormone peptide fragment

<400> SEQUENCE: 16

Asn Ser Met Glu Arg Val Glu Trp Leu Arg Lys Lys Leu Gln Asp Val
 1               5                  10                  15

His Asn Phe Val Ala Leu Gly Ala Pro Leu Ala Pro Arg Asp Ala Gly
             20                  25                  30

Ser Gln Arg Pro Arg Lys Lys Glu Asp Asn Val Leu Val Glu Ser His
         35                  40                  45

Glu Lys Ser Leu Gly Glu Ala Asp Lys Ala Asp Val Asn Val Leu Thr
     50                  55                  60

Lys Ala Lys Ser Gln
 65

<210> SEQ ID NO 17
<211> LENGTH: 68
<212> TYPE: PRT
<213> ORGANISM: Homo sapiens
<220> FEATURE:
<221> NAME/KEY: PEPTIDE
<222> LOCATION: (1)...(68)
<223> OTHER INFORMATION: human parathyroid hormone peptide fragment

<400> SEQUENCE: 17

Ser Met Glu Arg Val Glu Trp Leu Arg Lys Lys Leu Gln Asp Val His
 1               5                  10                  15

Asn Phe Val Ala Leu Gly Ala Pro Leu Ala Pro Arg Asp Ala Gly Ser
             20                  25                  30

Gln Arg Pro Arg Lys Lys Glu Asp Asn Val Leu Val Glu Ser His Glu
         35                  40                  45

Lys Ser Leu Gly Glu Ala Asp Lys Ala Asp Val Asn Val Leu Thr Lys
     50                  55                  60

Ala Lys Ser Gln
 65

<210> SEQ ID NO 18
<211> LENGTH: 67
<212> TYPE: PRT
<213> ORGANISM: Homo sapiens
<220> FEATURE:
<221> NAME/KEY: PEPTIDE
<222> LOCATION: (1)...(67)
<223> OTHER INFORMATION: human parathyroid hormone peptide fragment

<400> SEQUENCE: 18

Met Glu Arg Val Glu Trp Leu Arg Lys Lys Leu Gln Asp Val His Asn
 1               5                  10                  15

Phe Val Ala Leu Gly Ala Pro Leu Ala Pro Arg Asp Ala Gly Ser Gln
             20                  25                  30

Arg Pro Arg Lys Lys Glu Asp Asn Val Leu Val Glu Ser His Glu Lys
         35                  40                  45

Ser Leu Gly Glu Ala Asp Lys Ala Asp Val Asn Val Leu Thr Lys Ala
     50                  55                  60

Lys Ser Gln
 65
```

```
<210> SEQ ID NO 19
<211> LENGTH: 66
<212> TYPE: PRT
<213> ORGANISM: Homo sapiens
<220> FEATURE:
<221> NAME/KEY: PEPTIDE
<222> LOCATION: (1)...(66)
<223> OTHER INFORMATION: human parathyroid hormone peptide fragment

<400> SEQUENCE: 19

Glu Arg Val Glu Trp Leu Arg Lys Lys Leu Gln Asp Val His Asn Phe
 1               5                  10                  15

Val Ala Leu Gly Ala Pro Leu Ala Pro Arg Asp Ala Gly Ser Gln Arg
            20                  25                  30

Pro Arg Lys Lys Glu Asp Asn Val Leu Val Glu Ser His Glu Lys Ser
        35                  40                  45

Leu Gly Glu Ala Asp Lys Ala Asp Val Asn Val Leu Thr Lys Ala Lys
    50                  55                  60

Ser Gln
65

<210> SEQ ID NO 20
<211> LENGTH: 65
<212> TYPE: PRT
<213> ORGANISM: Homo sapiens
<220> FEATURE:
<221> NAME/KEY: PEPTIDE
<222> LOCATION: (1)...(65)
<223> OTHER INFORMATION: human parathyroid hormone peptide fragment

<400> SEQUENCE: 20

Arg Val Glu Trp Leu Arg Lys Lys Leu Gln Asp Val His Asn Phe Val
 1               5                  10                  15

Ala Leu Gly Ala Pro Leu Ala Pro Arg Asp Ala Gly Ser Gln Arg Pro
            20                  25                  30

Arg Lys Lys Glu Asp Asn Val Leu Val Glu Ser His Glu Lys Ser Leu
        35                  40                  45

Gly Glu Ala Asp Lys Ala Asp Val Asn Val Leu Thr Lys Ala Lys Ser
    50                  55                  60

Gln
65

<210> SEQ ID NO 21
<211> LENGTH: 64
<212> TYPE: PRT
<213> ORGANISM: Homo sapiens
<220> FEATURE:
<221> NAME/KEY: PEPTIDE
<222> LOCATION: (1)...(64)
<223> OTHER INFORMATION: human parathyroid hormone peptide fragment

<400> SEQUENCE: 21

Val Glu Trp Leu Arg Lys Lys Leu Gln Asp Val His Asn Phe Val Ala
 1               5                  10                  15

Leu Gly Ala Pro Leu Ala Pro Arg Asp Ala Gly Ser Gln Arg Pro Arg
            20                  25                  30

Lys Lys Glu Asp Asn Val Leu Val Glu Ser His Glu Lys Ser Leu Gly
        35                  40                  45

Glu Ala Asp Lys Ala Asp Val Asn Val Leu Thr Lys Ala Lys Ser Gln
    50                  55                  60
```

-continued

```
<210> SEQ ID NO 22
<211> LENGTH: 63
<212> TYPE: PRT
<213> ORGANISM: Homo sapiens
<220> FEATURE:
<221> NAME/KEY: PEPTIDE
<222> LOCATION: (1)...(63)
<223> OTHER INFORMATION: human parathyroid hormone peptide fragment

<400> SEQUENCE: 22

Glu Trp Leu Arg Lys Lys Leu Gln Asp Val His Asn Phe Val Ala Leu
 1               5                  10                  15

Gly Ala Pro Leu Ala Pro Arg Asp Ala Gly Ser Gln Arg Pro Arg Lys
            20                  25                  30

Lys Glu Asp Asn Val Leu Val Glu Ser His Glu Lys Ser Leu Gly Glu
        35                  40                  45

Ala Asp Lys Ala Asp Val Asn Val Leu Thr Lys Ala Lys Ser Gln
    50                  55                  60

<210> SEQ ID NO 23
<211> LENGTH: 62
<212> TYPE: PRT
<213> ORGANISM: Homo sapiens
<220> FEATURE:
<221> NAME/KEY: PEPTIDE
<222> LOCATION: (1)...(62)
<223> OTHER INFORMATION: human parathyroid hormone peptide fragment

<400> SEQUENCE: 23

Trp Leu Arg Lys Lys Leu Gln Asp Val His Asn Phe Val Ala Leu Gly
 1               5                  10                  15

Ala Pro Leu Ala Pro Arg Asp Ala Gly Ser Gln Arg Pro Arg Lys Lys
            20                  25                  30

Glu Asp Asn Val Leu Val Glu Ser His Glu Lys Ser Leu Gly Glu Ala
        35                  40                  45

Asp Lys Ala Asp Val Asn Val Leu Thr Lys Ala Lys Ser Gln
    50                  55                  60

<210> SEQ ID NO 24
<211> LENGTH: 61
<212> TYPE: PRT
<213> ORGANISM: Homo sapiens
<220> FEATURE:
<221> NAME/KEY: PEPTIDE
<222> LOCATION: (1)...(61)
<223> OTHER INFORMATION: human parathyroid hormone peptide fragment

<400> SEQUENCE: 24

Leu Arg Lys Lys Leu Gln Asp Val His Asn Phe Val Ala Leu Gly Ala
 1               5                  10                  15

Pro Leu Ala Pro Arg Asp Ala Gly Ser Gln Arg Pro Arg Lys Lys Glu
            20                  25                  30

Asp Asn Val Leu Val Glu Ser His Glu Lys Ser Leu Gly Glu Ala Asp
        35                  40                  45

Lys Ala Asp Val Asn Val Leu Thr Lys Ala Lys Ser Gln
    50                  55                  60

<210> SEQ ID NO 25
<211> LENGTH: 60
<212> TYPE: PRT
<213> ORGANISM: Homo sapiens
```

```
<220> FEATURE:
<221> NAME/KEY: PEPTIDE
<222> LOCATION: (1)...(60)
<223> OTHER INFORMATION: human parathyroid hormone peptide fragment

<400> SEQUENCE: 25

Arg Lys Lys Leu Gln Asp Val His Asn Phe Val Ala Leu Gly Ala Pro
 1               5                  10                  15

Leu Ala Pro Arg Asp Ala Gly Ser Gln Arg Pro Arg Lys Lys Glu Asp
                20                  25                  30

Asn Val Leu Val Glu Ser His Glu Lys Ser Leu Gly Glu Ala Asp Lys
                35                  40                  45

Ala Asp Val Asn Val Leu Thr Lys Ala Lys Ser Gln
    50                  55                  60

<210> SEQ ID NO 26
<211> LENGTH: 59
<212> TYPE: PRT
<213> ORGANISM: Homo sapiens
<220> FEATURE:
<221> NAME/KEY: PEPTIDE
<222> LOCATION: (1)...(59)
<223> OTHER INFORMATION: human parathyroid hormone peptide fragment

<400> SEQUENCE: 26

Lys Lys Leu Gln Asp Val His Asn Phe Val Ala Leu Gly Ala Pro Leu
 1               5                  10                  15

Ala Pro Arg Asp Ala Gly Ser Gln Arg Pro Arg Lys Lys Glu Asp Asn
                20                  25                  30

Val Leu Val Glu Ser His Glu Lys Ser Leu Gly Glu Ala Asp Lys Ala
                35                  40                  45

Asp Val Asn Val Leu Thr Lys Ala Lys Ser Gln
    50                  55

<210> SEQ ID NO 27
<211> LENGTH: 58
<212> TYPE: PRT
<213> ORGANISM: Homo sapiens
<220> FEATURE:
<221> NAME/KEY: PEPTIDE
<222> LOCATION: (1)...(58)
<223> OTHER INFORMATION: human parathyroid hormone peptide fragment

<400> SEQUENCE: 27

Lys Leu Gln Asp Val His Asn Phe Val Ala Leu Gly Ala Pro Leu Ala
 1               5                  10                  15

Pro Arg Asp Ala Gly Ser Gln Arg Pro Arg Lys Lys Glu Asp Asn Val
                20                  25                  30

Leu Val Glu Ser His Glu Lys Ser Leu Gly Glu Ala Asp Lys Ala Asp
                35                  40                  45

Val Asn Val Leu Thr Lys Ala Lys Ser Gln
    50                  55

<210> SEQ ID NO 28
<211> LENGTH: 57
<212> TYPE: PRT
<213> ORGANISM: Homo sapiens
<220> FEATURE:
<221> NAME/KEY: PEPTIDE
<222> LOCATION: (1)...(57)
<223> OTHER INFORMATION: human parathyroid hormone peptide fragment
```

```
<400> SEQUENCE: 28

Leu Gln Asp Val His Asn Phe Val Ala Leu Gly Ala Pro Leu Ala Pro
  1               5                  10                  15

Arg Asp Ala Gly Ser Gln Arg Pro Arg Lys Lys Glu Asp Asn Val Leu
                 20                  25                  30

Val Glu Ser His Glu Lys Ser Leu Gly Glu Ala Asp Lys Ala Asp Val
             35                  40                  45

Asn Val Leu Thr Lys Ala Lys Ser Gln
         50                  55

<210> SEQ ID NO 29
<211> LENGTH: 56
<212> TYPE: PRT
<213> ORGANISM: Homo sapiens
<220> FEATURE:
<221> NAME/KEY: PEPTIDE
<222> LOCATION: (1)...(56)
<223> OTHER INFORMATION: human parathyroid hormone peptide fragment

<400> SEQUENCE: 29

Gln Asp Val His Asn Phe Val Ala Leu Gly Ala Pro Leu Ala Pro Arg
  1               5                  10                  15

Asp Ala Gly Ser Gln Arg Pro Arg Lys Lys Glu Asp Asn Val Leu Val
                 20                  25                  30

Glu Ser His Glu Lys Ser Leu Gly Glu Ala Asp Lys Ala Asp Val Asn
             35                  40                  45

Val Leu Thr Lys Ala Lys Ser Gln
         50                  55

<210> SEQ ID NO 30
<211> LENGTH: 55
<212> TYPE: PRT
<213> ORGANISM: Homo sapiens
<220> FEATURE:
<221> NAME/KEY: PEPTIDE
<222> LOCATION: (1)...(55)
<223> OTHER INFORMATION: human parathyroid hormone peptide fragment

<400> SEQUENCE: 30

Asp Val His Asn Phe Val Ala Leu Gly Ala Pro Leu Ala Pro Arg Asp
  1               5                  10                  15

Ala Gly Ser Gln Arg Pro Arg Lys Lys Glu Asp Asn Val Leu Val Glu
                 20                  25                  30

Ser His Glu Lys Ser Leu Gly Glu Ala Asp Lys Ala Asp Val Asn Val
             35                  40                  45

Leu Thr Lys Ala Lys Ser Gln
         50                  55

<210> SEQ ID NO 31
<211> LENGTH: 54
<212> TYPE: PRT
<213> ORGANISM: Homo sapiens
<220> FEATURE:
<221> NAME/KEY: PEPTIDE
<222> LOCATION: (1)...(54)
<223> OTHER INFORMATION: human parathyroid hormone peptide fragment

<400> SEQUENCE: 31

Val His Asn Phe Val Ala Leu Gly Ala Pro Leu Ala Pro Arg Asp Ala
  1               5                  10                  15

Gly Ser Gln Arg Pro Arg Lys Lys Glu Asp Asn Val Leu Val Glu Ser
                 20                  25                  30
```

His Glu Lys Ser Leu Gly Glu Ala Asp Lys Ala Asp Val Asn Val Leu
            35                  40                  45

Thr Lys Ala Lys Ser Gln
        50

<210> SEQ ID NO 32
<211> LENGTH: 53
<212> TYPE: PRT
<213> ORGANISM: Homo sapiens
<220> FEATURE:
<221> NAME/KEY: PEPTIDE
<222> LOCATION: (1)...(53)
<223> OTHER INFORMATION: human parathyroid hormone peptide fragment

<400> SEQUENCE: 32

His Asn Phe Val Ala Leu Gly Ala Pro Leu Ala Pro Arg Asp Ala Gly
 1               5                  10                  15

Ser Gln Arg Pro Arg Lys Lys Glu Asp Asn Val Leu Val Glu Ser His
            20                  25                  30

Glu Lys Ser Leu Gly Glu Ala Asp Lys Ala Asp Val Asn Val Leu Thr
            35                  40                  45

Lys Ala Lys Ser Gln
        50

<210> SEQ ID NO 33
<211> LENGTH: 52
<212> TYPE: PRT
<213> ORGANISM: Homo sapiens
<220> FEATURE:
<221> NAME/KEY: PEPTIDE
<222> LOCATION: (1)...(52)
<223> OTHER INFORMATION: human parathyroid hormone peptide fragment

<400> SEQUENCE: 33

Asn Phe Val Ala Leu Gly Ala Pro Leu Ala Pro Arg Asp Ala Gly Ser
 1               5                  10                  15

Gln Arg Pro Arg Lys Lys Glu Asp Asn Val Leu Val Glu Ser His Glu
            20                  25                  30

Lys Ser Leu Gly Glu Ala Asp Lys Ala Asp Val Asn Val Leu Thr Lys
            35                  40                  45

Ala Lys Ser Gln
        50

<210> SEQ ID NO 34
<211> LENGTH: 51
<212> TYPE: PRT
<213> ORGANISM: Homo sapiens
<220> FEATURE:
<221> NAME/KEY: PEPTIDE
<222> LOCATION: (1)...(51)
<223> OTHER INFORMATION: human parathyroid hormone peptide fragment

<400> SEQUENCE: 34

Phe Val Ala Leu Gly Ala Pro Leu Ala Pro Arg Asp Ala Gly Ser Gln
 1               5                  10                  15

Arg Pro Arg Lys Lys Glu Asp Asn Val Leu Val Glu Ser His Glu Lys
            20                  25                  30

Ser Leu Gly Glu Ala Asp Lys Ala Asp Val Asn Val Leu Thr Lys Ala
            35                  40                  45

Lys Ser Gln
        50

```
<210> SEQ ID NO 35
<211> LENGTH: 50
<212> TYPE: PRT
<213> ORGANISM: Homo sapiens
<220> FEATURE:
<221> NAME/KEY: PEPTIDE
<222> LOCATION: (1)...(50)
<223> OTHER INFORMATION: human parathyroid hormone peptide fragment

<400> SEQUENCE: 35

Val Ala Leu Gly Ala Pro Leu Ala Pro Arg Asp Ala Gly Ser Gln Arg
 1               5                  10                  15

Pro Arg Lys Lys Glu Asp Asn Val Leu Val Glu Ser His Glu Lys Ser
            20                  25                  30

Leu Gly Glu Ala Asp Lys Ala Asp Val Asn Val Leu Thr Lys Ala Lys
        35                  40                  45

Ser Gln
    50

<210> SEQ ID NO 36
<211> LENGTH: 49
<212> TYPE: PRT
<213> ORGANISM: Homo sapiens
<220> FEATURE:
<221> NAME/KEY: PEPTIDE
<222> LOCATION: (1)...(49)
<223> OTHER INFORMATION: human parathyroid hormone peptide fragment

<400> SEQUENCE: 36

Ala Leu Gly Ala Pro Leu Ala Pro Arg Asp Ala Gly Ser Gln Arg Pro
 1               5                  10                  15

Arg Lys Lys Glu Asp Asn Val Leu Val Glu Ser His Glu Lys Ser Leu
            20                  25                  30

Gly Glu Ala Asp Lys Ala Asp Val Asn Val Leu Thr Lys Ala Lys Ser
        35                  40                  45

Gln

<210> SEQ ID NO 37
<211> LENGTH: 48
<212> TYPE: PRT
<213> ORGANISM: Homo sapiens
<220> FEATURE:
<221> NAME/KEY: PEPTIDE
<222> LOCATION: (1)...(48)
<223> OTHER INFORMATION: human parathyroid hormone peptide fragment

<400> SEQUENCE: 37

Leu Gly Ala Pro Leu Ala Pro Arg Asp Ala Gly Ser Gln Arg Pro Arg
 1               5                  10                  15

Lys Lys Glu Asp Asn Val Leu Val Glu Ser His Glu Lys Ser Leu Gly
            20                  25                  30

Glu Ala Asp Lys Ala Asp Val Asn Val Leu Thr Lys Ala Lys Ser Gln
        35                  40                  45

<210> SEQ ID NO 38
<211> LENGTH: 47
<212> TYPE: PRT
<213> ORGANISM: Homo sapiens
<220> FEATURE:
<221> NAME/KEY: PEPTIDE
<222> LOCATION: (1)...(47)
<223> OTHER INFORMATION: human parathyroid hormone peptide fragment
```

-continued

<400> SEQUENCE: 38

Gly Ala Pro Leu Ala Pro Arg Asp Ala Gly Ser Gln Arg Pro Arg Lys
1               5                   10                  15

Lys Glu Asp Asn Val Leu Val Glu Ser His Glu Lys Ser Leu Gly Glu
            20                  25                  30

Ala Asp Lys Ala Asp Val Asn Val Leu Thr Lys Ala Lys Ser Gln
        35                  40                  45

<210> SEQ ID NO 39
<211> LENGTH: 46
<212> TYPE: PRT
<213> ORGANISM: Homo sapiens
<220> FEATURE:
<221> NAME/KEY: PEPTIDE
<222> LOCATION: (1)...(46)
<223> OTHER INFORMATION: human parathyroid hormone peptide fragment

<400> SEQUENCE: 39

Ala Pro Leu Ala Pro Arg Asp Ala Gly Ser Gln Arg Pro Arg Lys Lys
1               5                   10                  15

Glu Asp Asn Val Leu Val Glu Ser His Glu Lys Ser Leu Gly Glu Ala
            20                  25                  30

Asp Lys Ala Asp Val Asn Val Leu Thr Lys Ala Lys Ser Gln
        35                  40                  45

<210> SEQ ID NO 40
<211> LENGTH: 45
<212> TYPE: PRT
<213> ORGANISM: Homo sapiens
<220> FEATURE:
<221> NAME/KEY: PEPTIDE
<222> LOCATION: (1)...(45)
<223> OTHER INFORMATION: human parathyroid hormone peptide fragment

<400> SEQUENCE: 40

Pro Leu Ala Pro Arg Asp Ala Gly Ser Gln Arg Pro Arg Lys Lys Glu
1               5                   10                  15

Asp Asn Val Leu Val Glu Ser His Glu Lys Ser Leu Gly Glu Ala Asp
            20                  25                  30

Lys Ala Asp Val Asn Val Leu Thr Lys Ala Lys Ser Gln
        35                  40                  45

<210> SEQ ID NO 41
<211> LENGTH: 44
<212> TYPE: PRT
<213> ORGANISM: Homo sapiens
<220> FEATURE:
<221> NAME/KEY: PEPTIDE
<222> LOCATION: (1)...(44)
<223> OTHER INFORMATION: human parathyroid hormone peptide fragment

<400> SEQUENCE: 41

Leu Ala Pro Arg Asp Ala Gly Ser Gln Arg Pro Arg Lys Lys Glu Asp
1               5                   10                  15

Asn Val Leu Val Glu Ser His Glu Lys Ser Leu Gly Glu Ala Asp Lys
            20                  25                  30

Ala Asp Val Asn Val Leu Thr Lys Ala Lys Ser Gln
        35                  40

<210> SEQ ID NO 42
<211> LENGTH: 43
<212> TYPE: PRT
<213> ORGANISM: Homo sapiens

```
<220> FEATURE:
<221> NAME/KEY: PEPTIDE
<222> LOCATION: (1)...(43)
<223> OTHER INFORMATION: human parathyroid hormone peptide fragment

<400> SEQUENCE: 42

Ala Pro Arg Asp Ala Gly Ser Gln Arg Pro Arg Lys Lys Glu Asp Asn
1               5                   10                  15

Val Leu Val Glu Ser His Glu Lys Ser Leu Gly Glu Ala Asp Lys Ala
            20                  25                  30

Asp Val Asn Val Leu Thr Lys Ala Lys Ser Gln
        35                  40

<210> SEQ ID NO 43
<211> LENGTH: 42
<212> TYPE: PRT
<213> ORGANISM: Homo sapiens
<220> FEATURE:
<221> NAME/KEY: PEPTIDE
<222> LOCATION: (1)...(42)
<223> OTHER INFORMATION: human parathyroid hormone peptide fragment

<400> SEQUENCE: 43

Pro Arg Asp Ala Gly Ser Gln Arg Pro Arg Lys Lys Glu Asp Asn Val
1               5                   10                  15

Leu Val Glu Ser His Glu Lys Ser Leu Gly Glu Ala Asp Lys Ala Asp
            20                  25                  30

Val Asn Val Leu Thr Lys Ala Lys Ser Gln
        35                  40

<210> SEQ ID NO 44
<211> LENGTH: 41
<212> TYPE: PRT
<213> ORGANISM: Homo sapiens
<220> FEATURE:
<221> NAME/KEY: PEPTIDE
<222> LOCATION: (1)...(41)
<223> OTHER INFORMATION: human parathyroid hormone peptide fragment

<400> SEQUENCE: 44

Arg Asp Ala Gly Ser Gln Arg Pro Arg Lys Lys Glu Asp Asn Val Leu
1               5                   10                  15

Val Glu Ser His Glu Lys Ser Leu Gly Glu Ala Asp Lys Ala Asp Val
            20                  25                  30

Asn Val Leu Thr Lys Ala Lys Ser Gln
        35                  40

<210> SEQ ID NO 45
<211> LENGTH: 40
<212> TYPE: PRT
<213> ORGANISM: Homo sapiens
<220> FEATURE:
<221> NAME/KEY: PEPTIDE
<222> LOCATION: (1)...(40)
<223> OTHER INFORMATION: human parathyroid hormone peptide fragment

<400> SEQUENCE: 45

Asp Ala Gly Ser Gln Arg Pro Arg Lys Lys Glu Asp Asn Val Leu Val
1               5                   10                  15

Glu Ser His Glu Lys Ser Leu Gly Glu Ala Asp Lys Ala Asp Val Asn
            20                  25                  30

Val Leu Thr Lys Ala Lys Ser Gln
        35                  40
```

```
<210> SEQ ID NO 46
<211> LENGTH: 39
<212> TYPE: PRT
<213> ORGANISM: Homo sapiens
<220> FEATURE:
<221> NAME/KEY: PEPTIDE
<222> LOCATION: (1)...(39)
<223> OTHER INFORMATION: human parathyroid hormone peptide fragment

<400> SEQUENCE: 46

Ala Gly Ser Gln Arg Pro Arg Lys Lys Glu Asp Asn Val Leu Val Glu
 1               5                  10                  15

Ser His Glu Lys Ser Leu Gly Glu Ala Asp Lys Ala Asp Val Asn Val
                20                  25                  30

Leu Thr Lys Ala Lys Ser Gln
        35

<210> SEQ ID NO 47
<211> LENGTH: 38
<212> TYPE: PRT
<213> ORGANISM: Homo sapiens
<220> FEATURE:
<221> NAME/KEY: PEPTIDE
<222> LOCATION: (1)...(38)
<223> OTHER INFORMATION: human parathyroid hormone peptide fragment

<400> SEQUENCE: 47

Gly Ser Gln Arg Pro Arg Lys Lys Glu Asp Asn Val Leu Val Glu Ser
 1               5                  10                  15

His Glu Lys Ser Leu Gly Glu Ala Asp Lys Ala Asp Val Asn Val Leu
                20                  25                  30

Thr Lys Ala Lys Ser Gln
        35

<210> SEQ ID NO 48
<211> LENGTH: 37
<212> TYPE: PRT
<213> ORGANISM: Homo sapiens
<220> FEATURE:
<221> NAME/KEY: PEPTIDE
<222> LOCATION: (1)...(37)
<223> OTHER INFORMATION: human parathyroid hormone peptide fragment

<400> SEQUENCE: 48

Ser Gln Arg Pro Arg Lys Lys Glu Asp Asn Val Leu Val Glu Ser His
 1               5                  10                  15

Glu Lys Ser Leu Gly Glu Ala Asp Lys Ala Asp Val Asn Val Leu Thr
                20                  25                  30

Lys Ala Lys Ser Gln
        35

<210> SEQ ID NO 49
<211> LENGTH: 36
<212> TYPE: PRT
<213> ORGANISM: Homo sapiens
<220> FEATURE:
<221> NAME/KEY: PEPTIDE
<222> LOCATION: (1)...(36)
<223> OTHER INFORMATION: human parathyroid hormone peptide fragment

<400> SEQUENCE: 49

Gln Arg Pro Arg Lys Lys Glu Asp Asn Val Leu Val Glu Ser His Glu
 1               5                  10                  15
```

Lys Ser Leu Gly Glu Ala Asp Lys Ala Asp Val Asn Val Leu Thr Lys
            20                  25                  30

Ala Lys Ser Gln
        35

<210> SEQ ID NO 50
<211> LENGTH: 35
<212> TYPE: PRT
<213> ORGANISM: Homo sapiens
<220> FEATURE:
<221> NAME/KEY: PEPTIDE
<222> LOCATION: (1)...(35)
<223> OTHER INFORMATION: human parathyroid hormone peptide fragment

<400> SEQUENCE: 50

Arg Pro Arg Lys Lys Glu Asp Asn Val Leu Val Glu Ser His Glu Lys
1               5                   10                  15

Ser Leu Gly Glu Ala Asp Lys Ala Asp Val Asn Val Leu Thr Lys Ala
            20                  25                  30

Lys Ser Gln
        35

<210> SEQ ID NO 51
<211> LENGTH: 34
<212> TYPE: PRT
<213> ORGANISM: Homo sapiens
<220> FEATURE:
<221> NAME/KEY: PEPTIDE
<222> LOCATION: (1)...(34)
<223> OTHER INFORMATION: human parathyroid hormone peptide fragment

<400> SEQUENCE: 51

Pro Arg Lys Lys Glu Asp Asn Val Leu Val Glu Ser His Glu Lys Ser
1               5                   10                  15

Leu Gly Glu Ala Asp Lys Ala Asp Val Asn Val Leu Thr Lys Ala Lys
            20                  25                  30

Ser Gln

<210> SEQ ID NO 52
<211> LENGTH: 33
<212> TYPE: PRT
<213> ORGANISM: Homo sapiens
<220> FEATURE:
<221> NAME/KEY: PEPTIDE
<222> LOCATION: (1)...(33)
<223> OTHER INFORMATION: human parathyroid hormone peptide fragment

<400> SEQUENCE: 52

Arg Lys Lys Glu Asp Asn Val Leu Val Glu Ser His Glu Lys Ser Leu
1               5                   10                  15

Gly Glu Ala Asp Lys Ala Asp Val Asn Val Leu Thr Lys Ala Lys Ser
            20                  25                  30

Gln

<210> SEQ ID NO 53
<211> LENGTH: 32
<212> TYPE: PRT
<213> ORGANISM: Homo sapiens
<220> FEATURE:
<221> NAME/KEY: PEPTIDE
<222> LOCATION: (1)...(32)
<223> OTHER INFORMATION: human parathyroid hormone peptide fragment

```
                              -continued
<400> SEQUENCE: 53

Lys Lys Glu Asp Asn Val Leu Val Glu Ser His Glu Lys Ser Leu Gly
1               5                   10                  15

Glu Ala Asp Lys Ala Asp Val Asn Val Leu Thr Lys Ala Lys Ser Gln
            20                  25                  30
```